US009492081B2

(12) United States Patent
Henry et al.

(10) Patent No.: US 9,492,081 B2
(45) Date of Patent: Nov. 15, 2016

(54) APPARATUS AND METHOD FOR RETINAL MEASUREMENT

(71) Applicant: THE SCIENCE AND TECHNOLOGY FACILITIES COUNCIL, Daresbury, Warrington (GB)

(72) Inventors: David Henry, Edinburgh (GB); Tom Margrain, Cardiff (GB); Alison Binns, Cardiff (GB); David Atkinson, Edinburgh (GB); Stephen Todd, Edinburgh (GB)

(73) Assignee: The Science and Technology Facilities Council, Daresbury, Warrington (GB)

( * ) Notice: Subject to any disclaimer, the term of this patent is extended or adjusted under 35 U.S.C. 154(b) by 126 days.

(21) Appl. No.: 14/389,815

(22) PCT Filed: Apr. 5, 2013

(86) PCT No.: PCT/GB2013/050887
§ 371 (c)(1),
(2) Date: Oct. 1, 2014

(87) PCT Pub. No.: WO2013/150310
PCT Pub. Date: Oct. 10, 2013

(65) Prior Publication Data
US 2015/0062530 A1    Mar. 5, 2015

(30) Foreign Application Priority Data
Apr. 5, 2012    (GB) .................................. 1206174.3

(51) Int. Cl.
*A61B 3/14*    (2006.01)
*A61B 3/12*    (2006.01)
(Continued)

(52) U.S. Cl.
CPC .............. *A61B 3/12* (2013.01); *A61B 3/0025* (2013.01); *A61B 3/063* (2013.01); *A61B 3/14* (2013.01)

(58) Field of Classification Search
CPC .. A61B 3/0008; A61B 3/0025; A61B 3/112; A61B 3/14; A61B 3/145
USPC .......................... 351/204, 205, 206, 221, 246
See application file for complete search history.

(56) References Cited

U.S. PATENT DOCUMENTS

| 2004/0087843 A1 | 5/2004 | Rice et al. | |
| 2007/0121071 A1* | 5/2007 | Jackson | A61B 3/0033 351/246 |
| 2008/0231804 A1* | 9/2008 | Gagne | A61B 3/12 351/208 |

FOREIGN PATENT DOCUMENTS

| EP | 1641386 A | 4/2000 |
| EP | 1100370 B | 5/2001 |

(Continued)

OTHER PUBLICATIONS

J. Van De Kratts et al, "The Pathways of Light Measured in Fundus Reflectometry," Vision Research, 1996, pp. 2229-2247, vol. 36 No. 15, Elsevier Science Ltd., GB.

(Continued)

*Primary Examiner* — Huy K Mai
(74) *Attorney, Agent, or Firm* — Barnes & Thornburg LLP

(57) ABSTRACT

Embodiments of the present invention provide a retinal densitometer, comprising an illumination unit for outputting bleaching illumination for photo-bleaching an eye and reflectance illumination at one or more wavelengths for determining reflectance of the eye at the one or more wavelengths, an imaging device arranged to output image data corresponding to an image of the eye at the one or more wavelengths of reflectance illumination, and a control unit arranged to control the illumination unit and the imaging device to output the bleaching illumination, the reflectance illumination at the one or more wavelengths and to output image data according to a predetermined sequence.

33 Claims, 6 Drawing Sheets

(51) Int. Cl.
*A61B 3/06* (2006.01)
*A61B 3/00* (2006.01)

(56) References Cited

FOREIGN PATENT DOCUMENTS

| WO | WO03/039332 | 5/2003 |
| WO | WO2007/053942 | 5/2007 |
| WO | 2005023094 A2 | 2/2008 |
| WO | 2013078412 A | 5/2013 |

OTHER PUBLICATIONS

H. Ripps et al., "Rhodopsin Regeneration in Man," Nature, May 24, 1969, pp. 775-777, vol. 222.
P. Kilbride et al, "Determination of Human Cone Pigment Density Difference Spectra in Spatially Resolved Regions of the Fovea," Vision Research, 1983, pp. 1341-1350, vol. 23, No. 12, Pergamon Press Ltd.
T. Berendschot et al., "Fundus Reflectance—Historical and Present Ideas," Progress in Retinal and Eye Research, 2003, pp. 171-200, vol. 22, Elsevier Science Ltd.
M. Alpern et al., "The Density and Photosensitivity of Human Rhodopsin in the Living Retina," Journal of Physiology, 1974, pp. 341-370, vol. 237.
M. Hammer et al., "Imaging Spectroscopy of the Human Ocular Fundus In Vivo," Journal of Biomedical Optics, Oct. 1997, pp. 418-425, vol. 2, No. 4.
A. Tumlinson et al., "Techniques for Extraction of Depth-Resolved In Vivo Human Retinal Intrinsic Optical Signals with Optical Coherence Tomography," Japanese Journal of Ophthalmology, 2009, pp. 315-326, vol. 53, Japanese Ophthalmogical Society.
T. Theelen et al., "Analysis of Visual Pigment by Fundus Autofluorescence," Experimental Eye Research, 2008, pp. 296-304, vol. 86, issue 2.
United Kingdom Intellectual Property Office, Search Report for GB1206174.3, Jul. 30, 2012, 3 pages.
D. Van Norren et al., "A Continuously Recording Retinal Densitometer," Vision Research, Oct. 2, 1980, pp. 897-905, vol. 21, No. 6, Pergamon Press, Oxford, GB.
D. Van Norren et al., "Retinal Densitometer with the Size of a Fundus Camera," Vision Research, Jul. 11, 1988, pp. 369-374, vol. 29, No. 3, Pergamon Press, Oxford, GB.
PCT Search Report and Written Opinion for PCT/GB2013/050887, completed Jul. 4, 2013.
Van Norren, Dirk, et al., "A Continuously Recording Retinal Densitometer", Vision Research, vol. 21, Issue 6, 1981, pp. 897-905, Abstract Only.
Van Norren, Dirk, et al., "Retinal Densitometer with the Size of a Fundus Camera", Vision Research, vol. 29, Issue 3, 1989, pp. 369-374, Abstract Only.

* cited by examiner

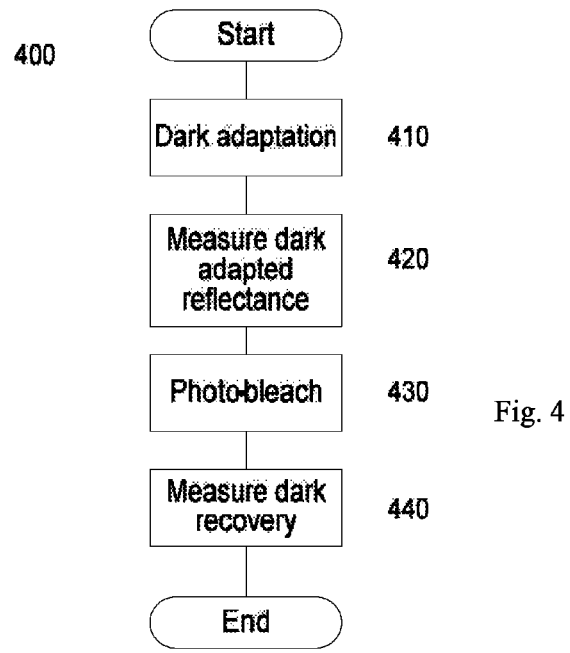
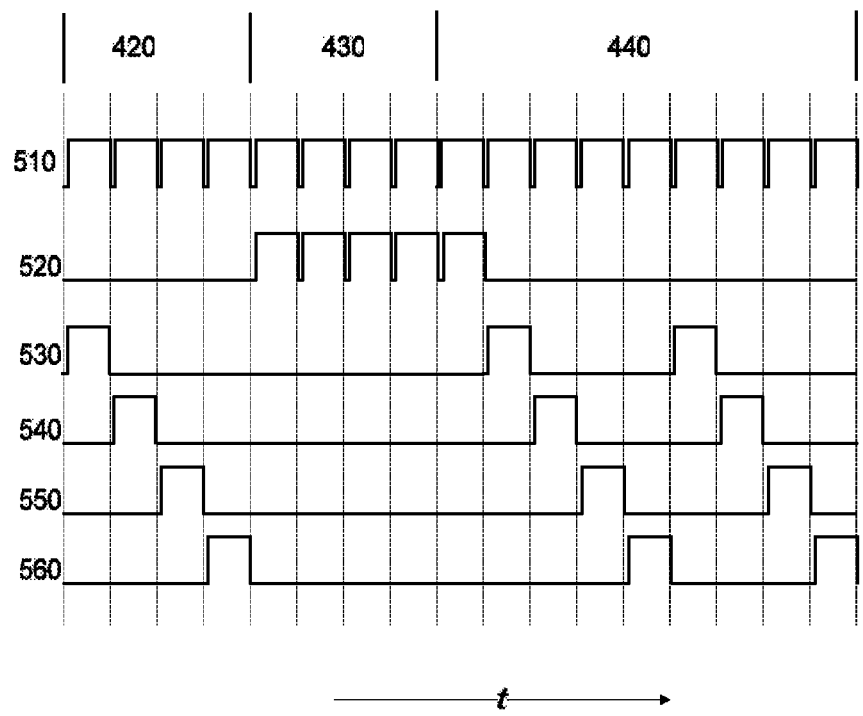

APPARATUS AND METHOD FOR RETINAL MEASUREMENT

CROSS REFERENCE TO RELATED APPLICATIONS

This application is a national stage entry under 35 U.S.C. §371 (b) of International Application No. PCT/GB2013/050887, which was filed Apr. 5, 2013, and which claims priority to United Kingdom patent application serial number 1206174.3 filed Apr. 5, 2012, the entire disclosure of which is incorporated by reference herein.

BACKGROUND

Blindness and poor vision affects about 920,000 people in the UK alone. In the UK most vision loss occurs with ageing and is related to disease in the retina at the back of the eye. The main disease is known as age related macular degeneration (AMD). In order to understand and potentially treat this and other conditions it is important to be able to identify the early signs of disease in the retina.

It is known that one early sign of such disease is a change in the way that the eye adapts to dark conditions after exposure to light.

It is an object of embodiments of the invention to provide an apparatus and method for measuring characteristics of the retina.

BRIEF DESCRIPTION OF THE DRAWINGS

Embodiments of the invention will now be described by way of example only, with reference to the accompanying figures, in which:

FIG. 4 illustrates a method according to a first embodiment of the invention; and FIG. 5 illustrates a timing diagram according to an embodiment of the invention;

DETAILED DESCRIPTION OF EMBODIMENTS OF THE INVENTION

Figure 1:
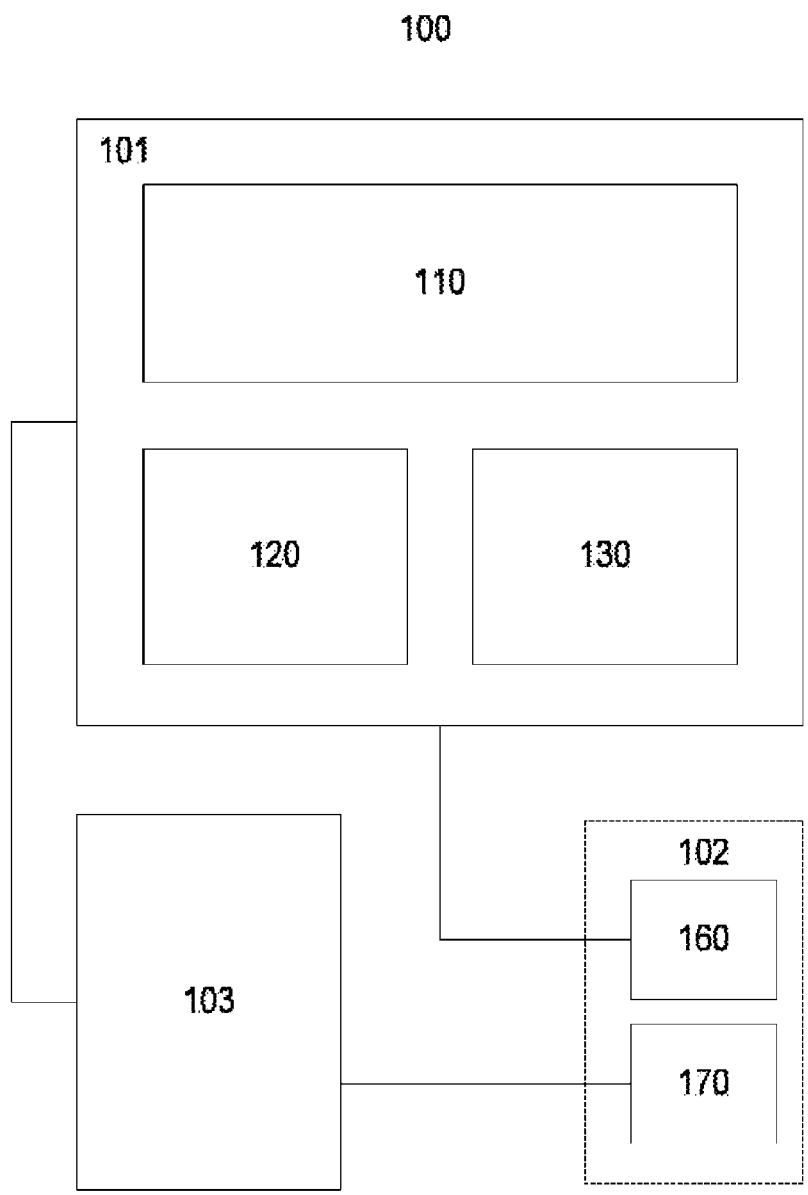
FIG. 1 shows an apparatus according to an embodiment of the invention.

FIG. 1 illustrates an apparatus 100 according to an embodiment of the invention. As illustrated in FIG. 1, the apparatus 100 comprises three units: a control unit 101, a head unit 102 and an analysis unit 103. It will be realised that the structure shown in FIG. 1 is merely illustrative and that other structures or arrangements of components may be envisaged. For example, the control unit 101 and analysis unit 103 may be formed as a single unit or the control 101, head 102 and analysis 103 units may be combined.

The control unit 101 comprises a control module 110 which, as will be explained, is arranged in some embodiments to synchronise light generation and image acquisition; a measurement module 120; and a bleaching module 130.

The measurement module 120 is arranged to generate illumination for measuring one or more characteristics of a patient's eye. In one embodiment the characteristic measured response to the illumination is a reflectance of the patient's eye. The generated illumination may be visible light. In particular, the measurement module 120 is arranged to output light of one or more predetermined wavelengths, or wavelength bands, such that the reflectance of the light at that wavelength from the patient's eye is determined, as will be explained.

The measurement module 120 is arranged to output light at one or more wavelengths. The one or more wavelength may be selected from amongst a plurality of wavelengths or wavelength bands. The intensity of each wavelength band may be independently controlled. Some embodiments of the invention are capable of outputting light at a plurality of wavelengths which may include 410, 440, 470, 500, 530, 560, 590, 620, 650, 680, 710, 740, 850 nm, although it will be realised that the number and choice of wavelengths is merely illustrative. The light output at each wavelength may have a predetermined bandwidth, such as a bandwidth of 10 nm at FWHM.

The measurement module 120 may comprise a plurality of light sources, such as LEDs, each having a predetermined wavelength. In order to limit or control the bandwidth of light output from each light source, each light source may be associated with a filter having a predetermined bandwidth. The wavelength of light output by the measurement module 120 may be selected from amongst the plurality of wavelengths according to a wavelength control signal received from the control module 110. The measurement module 120 may generate light having a luminance in the range of 2.6-4 log Troland (Td), although it will be realised that other luminance values may be envisaged. The reflectance unit 120 may be arranged to output light in pulses of a predetermined duration, such a predetermined duration of between 0.05 and 1 second, although it will be realised that other pulse durations may be envisaged. The intensity and duration of each pulse may be controlled in response to one or more control signals received from the control module 110.

Light output by the measurement module 120 is communicated to the head unit 102 to be directed into the patient's eye. The light may be communicated to the head unit 102 by one or more fibre optic cables. In some embodiments, each light source has a respective fibre optic cable for communicating light from the light source to the head unit 102. However other embodiments may be envisaged in which a plurality of light sources share a fibre optic cable or other light guide.

The bleaching module 130 is arranged to generate illumination for photo-bleaching the patient's retina. As will be explained, in a mode of operation according to a first embodiment, the bleaching may be substantially complete bleaching of the retina or, in a mode of operation according to a second embodiment, partial bleaching of the retina. The retina contains a number of visual pigments (e.g. rhodopsin) which are responsible for phototransduction in the retina. The visual pigments are sensitive to light and photo-bleaches responsive to illumination. It will be understood that the term retina may include one or more of the following structures within the eye: the optic nerve head, neural retina, retina pigment epithelium, choroid, sclera and vasculature supplying the retina.

The bleaching module 130 comprises a broadband light source. The broadband light source is arranged in some embodiments to generate light at a higher intensity than the measurement module 120. The bleaching module 130 may output light having a luminance of around 6 log Td, although it will be realised that other luminance values may be chosen which are sufficient to at least partly photo-bleach the retina. The bleaching module 130 may output light for a duration sufficient to photo bleach the retina, such as for a duration of between 2 and 30 minutes. In some embodiments bleaching module 130 is arranged to output light in pulses of a predetermined duration, such as a duration of between 5 ms and 120 seconds, sufficient to at least partially bleach the retina, although it will be realised that other pulse durations may be envisaged. The luminance and duration of each pulse may be controlled in response to one or more control signals received from the control module 110.

Light output by the bleaching module 130 is communicated to the head unit 102 for directing towards the patient's eye. The output light may communicated by one or more fibre optic cables to the head unit 102. In some embodiments a liquid light guide may be used to communicate light from the bleaching module 130 to the head unit 102. The liquid light guide may be used to provide a high degree of light throughput to the head unit 102.

The head unit 102 comprises optics 160 for directing light into the patient's eye, particularly in some embodiments toward the patient's retina, and receiving light reflected from the eye. The head unit 102 further comprises an imaging device 170 for recording an image of light reflected from the patient's eye and received through the optics 160. The image is based on light output from the measurement module 120, received by the eye and reflected to the imaging device 170.

Figure 2:
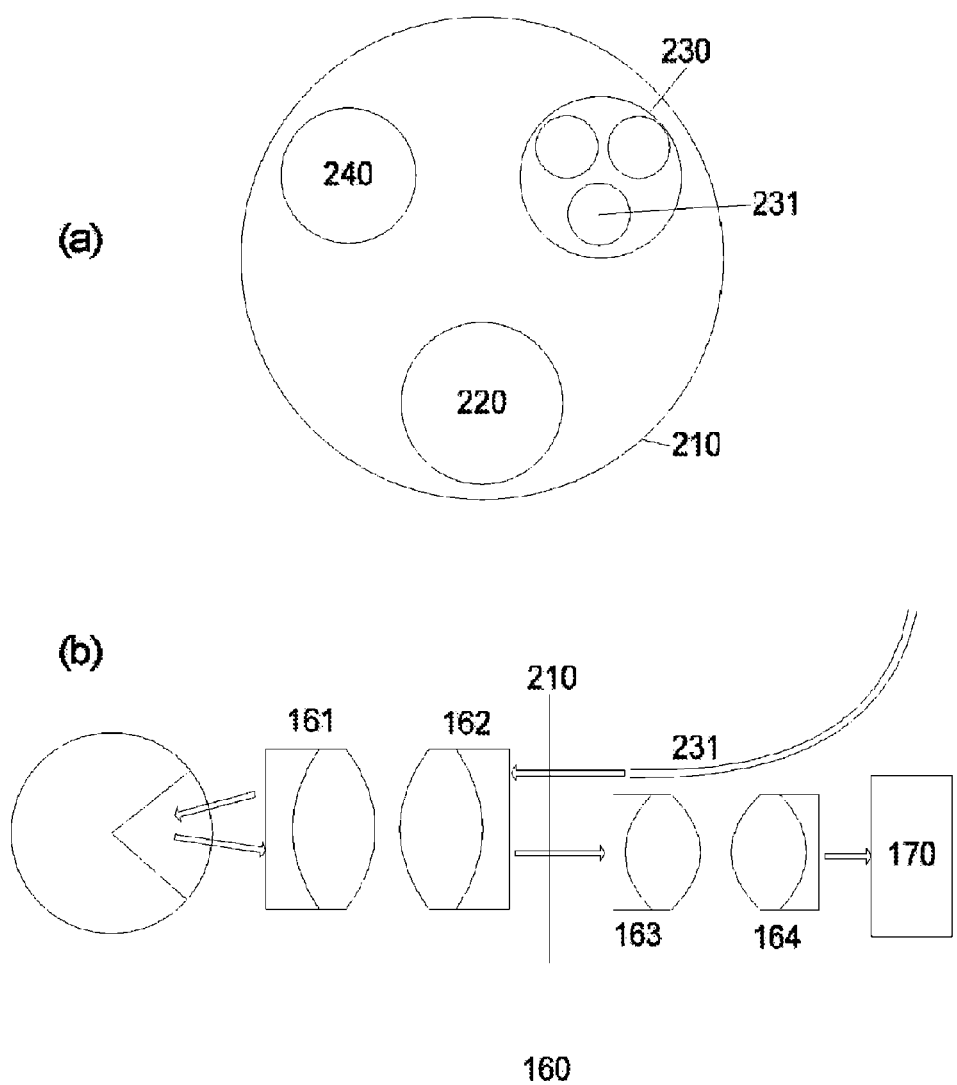
FIG. 2 shows an optical arrangement according to an embodiment of the invention.

The head unit 102 comprises an eyepiece arranged to form a magnified image of the pupil of the eye. Illumination (light introduced into the eye) and imaging use separate pupil images within the pupil of the eye. FIG. 2a illustrates a magnified pupil image 210 formed by the eyepiece. A portion of the eye's pupil is magnified by the eyepiece. The predetermined portion is, in some embodiments, 2.5 mm in diameter. This portion is magnified to form the magnified pupil image 210 shown in FIG. 2a. A magnification ratio of 6 is used in one embodiment, although it will be realised that other values may be chosen. At this magnification ratio the magnified pupil image 210 has a diameter of 15 mm. Within this magnified pupil image 210 is arranged an imaging pupil 220 from which light reflected by the retina will be imaged, a reflectance pupil 230 into which light from the measurement module 120 is introduced into the eye, and a bleaching pupil 240 into which light from the bleaching module 130 is introduced into the eye. Within the reflectance pupil 230 are arranged each of the fibre optic cables 231 (only one of which is indicated with a reference numeral for clarity) from the respective light sources in the measurement module 120. Whilst FIG. 2 includes representation of three fibre optic cables it will be realised that others may be included and the diagram is not to scale. For example, in embodiments where the measurement module 120 is capable of generating 12 wavelengths of light, there may be 12 corresponding fibre optic cables. In another embodiment, rather than having separate discrete fibre optic cables occupying a region of the reflectance pupil 230, the individual fibres may be brought together or fed into a light guide, such as a liquid light guide, prior to the head unit 102. In this way, all wavelengths of light are introduced into the same region of the eye within the reflectance pupil.

Whilst the pupil image shown in FIG. 2a includes discrete i.e. separate circular areas for introducing reflectance and bleaching illumination, and for imaging, it will be realised that the areas may be concentrically arranged in other embodiments. For example, the imaging area 220 may be central, the reflectance area 230 arranged around a periphery of the imaging area 220 and the bleaching area 240 around a periphery of the reflectance area. Advantageously this concentric arrangement may reduce the sensitivity to involuntary movements of the patient's eye affecting reflectance measurements.

FIG. 2b schematically illustrates a layout of the optics 160 according to an embodiment of the invention. The optics 160 direct light from the one or more fibre optic cables 231 (an end of one of the fibre optic cables 231 is shown) and the liquid light guide which emit light delivered from the reflecting and bleaching modules 120, 130 to the eye, and direct reflected light received from the eye to the imaging device 170.

The eyepiece may comprise first and second achromatic doublets 161, 162 arranged to form a modified Plössl eyepiece. In another embodiment, the eyepiece may comprise a single achromatic lens. The eyepiece forms an image of the pupil of the eye at the magnified pupil plane 210 at a predetermined distance, such as 170 mm, magnified by the magnification ratio of the lenses 161, 162. The optics 160 may further comprise a second pair of achromatic doublets 163, 164 which are arranged to form an image having a corresponding diameter to that of the imaging device 170. It will be realised that the optics 160 may comprise further components, such as black dot masks to prevent stray light and focussing optics, as will be appreciated by the skilled person.

The imaging device 170 is arranged to record an image of light reflected from the eye. The imaging device may be a CCD, a CMOS image sensor or other electronic device capable of outputting data representing an image of received light over a two dimensional area as will be appreciated by the skilled person. The imaging device 170 records a spatial map of received light from the imaging area of the magnified pupil such that an image of the reflected light may be produced.

In a particular embodiment of the invention the imaging device 170 is a frame transfer CCD which comprises a storage region of approximately half of the active area of the CCD covered by a mask. The remaining open half of the active area is an image region and is used to store charge corresponding to light impinging thereon, before the stored charge is transferred to the storage region for readout, conversion to digital values and corresponding output as image data, as will be appreciated. The imaging device 170 is arranged to the output image data indicative of light reflected by the eye in response to illumination from the reflectance or bleaching modules 120, 130. The imaging device may be a fundus camera in one embodiment.

Figure 3:
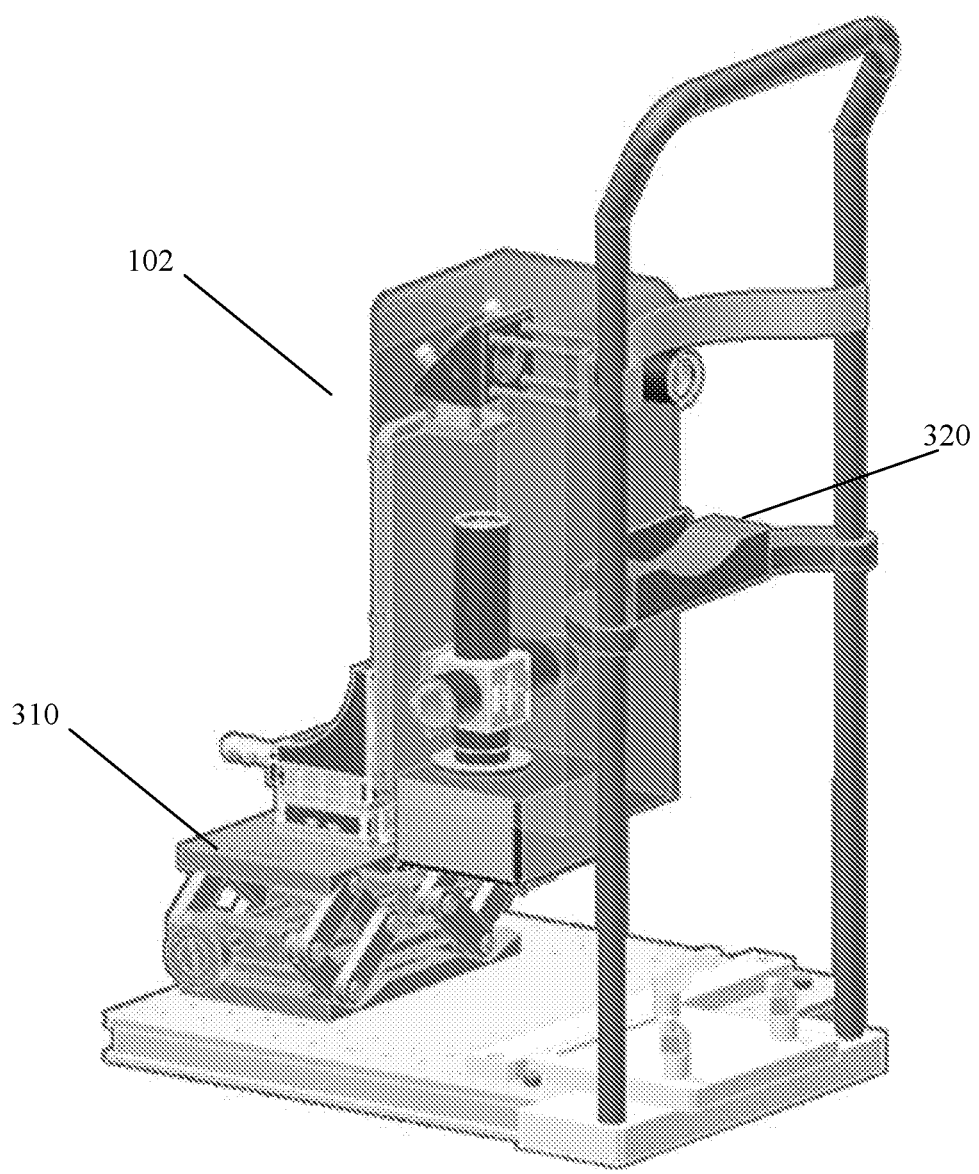
FIG. 3 shows a head unit according to an embodiment of the invention.

FIG. 3 is a perspective view of the head unit 102 according to an embodiment of the invention. The head unit 102 comprises the optics 160 and imaging device 170 shown in FIG. 2. The head unit 102 is moveable mounted upon an adjustment stage 310 which allows the position of the head unit 102 to be changed. A headrest 320 is provided for supporting the patient's head and allowing the position of the patient's head to be maintained in relation to the head unit 102 during use of the apparatus. The adjustment stage 310 allows the position of the head unit to be changed in x and y directions to obtain alignment between the lens eyepiece and the patient's eye 230. The position of the head unit may also be vertically controlled in a z direction.

Referring again to FIG. 1, as noted above, the apparatus comprises the analysis unit 103. The analysis unit 103 may be implemented as a general purpose computer, such as a PC, which is arranged to execute appropriate software, or may be a dedicated device comprising a suitable input unit for receiving an operator's input, such as a keyboard, and an output unit for displaying a result of the analysis of the patient's retina, such as a display screen. For the purposes of explanation the following description will be based on the analysis unit 103 being implemented as a computer, although it will be realised that this is exemplary.

The analysis unit 103 is arranged to execute an application program for controlling the apparatus 100. Via a graphical user interface of the application program the operator is able to select a mode of operation, such as from amongst the modes which will be explained with reference to FIGS. 4 to 9, and to commence execution of the operation. The application program may also allow the user to select one or a plurality of wavelengths at which the reflectivity of the eye will be measured and other parameters of the measurement process, as will be appreciated. The analysis unit 103 is communicably coupled to the control unit 101, such as via a USB connection, to output information indicative of the selected mode of operation, parameters associated therewith and commencement of the operation. The analysis unit 103 is also communicably coupled to the imaging device 170 to receive the output image data corresponding to the reflected light. The application program is further arranged to interpret and to display information on the display device based upon the image data, as will be explained.

A first method 400 of operation of the apparatus will now be explained with reference to FIGS. 4 and 5. The first method of operation is a densitometry measurement method. The densitometry method provides image data corresponding to a sequence of images from which the reflectance of the patient's retina at one or a plurality of illumination wavelengths may be spatially mapped over a period of time. In particular, the reflectance of the retina is spatially mapped during dark recovery of the retina. Some embodiments of the invention are further arranged to determine a spatially averaged variation in reflectance over time. FIG. 4 illustrates the method steps as a flow chart and FIG. 5 illustrates control signals in the apparatus 100 as will be explained.

In step 410 dark adaptation of the patient's eye is performed. During step 410 the eye is not subjected to substantial illumination. During dark adaptation rhodopsin in the eye regenerates and a sensitivity of the eye to light increases.

Following the period of dark adaptation in step 410, in step 420 the reflectance of the patient's retina is spatially mapped at one or more illumination wavelengths. In the illustrative example the reflectance of the eye will be mapped at four illumination wavelengths. It will be realised that the use of four illumination wavelengths is merely exemplary and that other numbers of illumination wavelengths may be used.

FIG. 5 illustrates a plurality of control signals within the apparatus. Signal 510 is an image transfer control signal provided to the imaging device 170. The image transfer signal is illustrated as active low. Whilst the image transfer signal is high light received by the imaging device 170 generates charge which is stored, thus the high image transfer signal corresponds to an image recording period of the imaging device 170. A low signal level causes a transfer of the stored charge to the storage region of the imaging device for subsequent readout, as will be appreciated by the skilled person. In some embodiments the image transfer signal 510 is caused to be periodically low for a period of around 0.9 ms to allow for charge transfer from the image region to the storage region. Based on this frame transfer time the imaging device 170 has a duty cycle of 99.1% for a 1 Hz readout.

Control signal 520 is provided to the bleaching module 130 to cause the output of high intensity illumination for photo-bleaching the retina. Signal 520 may be referred to as a bleaching signal 520 which is active high i.e. bleaching illumination is output when high.

Control signals 530-560 are provided to each of a plurality of reflectance light sources, such as LEDs, within the measurement module 120 to cause each light source to output a respective wavelength of light when the corresponding signal is high. These signals may be referred to as reflectance signals 530-560.

The apparatus is arranged as exemplified in FIG. 5 to operate at a 1 Hz period i.e. the imaging device 170 is controlled to output image data at 1 second intervals. However it will be realised that operation at 1 Hz is merely exemplary and that other operating frequencies may be chosen.

During step 420, each of the reflectance light sources controlled by the reflectance signals 530-560 are operably controlled to be sequentially active for a predetermined period whilst a corresponding image is recorded. For example, the first reflectance signal 530 is active (high) for the predetermined period of time thereby causing a corresponding first reflectance light source to output light of a predetermined wavelength whilst an image of reflected is recorded by the imaging device 170. The image transfer control signal 510 then become briefly active to allow the stored charge to be transferred to the storage portion of the CCD. Following which a second reflectance signal 540 is activated (high) to cause a second reflectance light source to output light of a predetermined second wavelength whilst a second reflectance image is recorded, and so on. Thus, in step 420 a dark adapted spatial map of light reflectance at each of a plurality of wavelengths is sequentially recorded. Embodiments of the invention may be envisaged wherein two or more reflectance light sources are simultaneously active whilst an image is recorded.

In order to allow observation and study of retinal behaviour on relatively short timescales in the order of seconds and milliseconds, in embodiments of the invention timing synchronisation between bleaching and reflectance measurement illumination and image capture is provided. The synchronisation may be achieved by having a master timing generator in the system which controls an operational timing of system components, such as light generation and image capture. In some embodiments, the timing generator is the control module 110 which outputs signals to control the timing of the measurement module 120, bleaching module 130 and imaging device 170. However, the timing signals may be output by another module or component of the system. In one embodiment, the timing signals may be generated by the imaging device 170 and provided to the measurement module 120 and bleaching module 130 to synchronise light generation with image capture, such that light generation and image capture is synchronised to a short timescale.

In step 430 the retina is photo-bleached whilst reflectance images of the retina are periodically captured by the imaging device 170. Photo-bleaching of the retina is performed utilising the bleaching module 130 which is caused to output wide-band illumination for a predetermined period of time, such as 30 seconds. In some embodiments, at periodic intervals during the photo-bleaching, images of the retina may, in some embodiments, be captured by momentarily causing the high intensity illumination unit 130 to cease whilst the charge stored in the imaging portion of the CCD is transferred to the storage portion by operation of the image transfer signal 510. Temporarily ceasing output of bleaching illumination prevents image "smearing" during the transfer process. It will be realised that embodiments may be envisaged wherein imagines are not captured during the photo-bleaching. Whilst FIG. 5 shows photo-bleaching for a period of four seconds (four operations of the image transfer signal at 1 Hz) it will be realised that in practical operation step 430 may continue for longer.

In step 440 dark recovery of the retina is allowed whilst images of the retina are periodically captured by the imaging device 170. In step 440 the bleaching module 130 is not operated whilst the measurement module 120 periodically generates low intensity light at one or more wavelengths in a predetermined sequence. Whilst the reflectance illumination at each wavelength is introduced to the eye, a corresponding image of the retina is captured by the imaging device 170, as in step 420. During step 440 in FIG. 5 a sequence of reflectance images is continually captured. That is, following low intensity illumination and corresponding image capture at a fourth wavelength in response to a fourth reflectance signal 560, illumination and image capture at the first wavelength in response to the first low intensity control signal 530 is immediately performed. However it will be realised that a predetermined delay may be introduced between sequences of reflectance illumination and corresponding image capture. For example, in FIG. 5 following the four second sequence of reflectance image capture at the four wavelengths, a delay of a predetermined period may be provided before the sequence of image capture is again performed. In step 440 an image at each wavelength is captured at a predetermined frequency during dark recovery.

Figure 6:
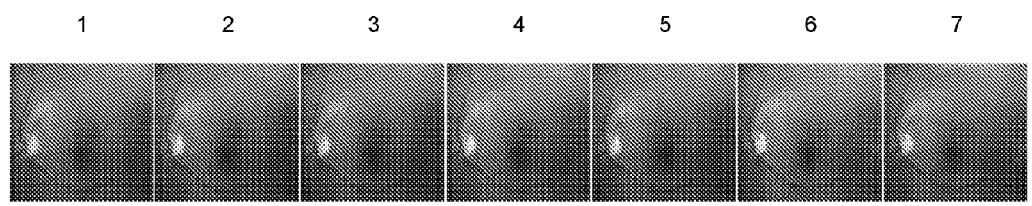
FIG. 6 illustrates a sequence of retinal images recorded by an embodiment of the invention following dark adaptation.
Figure 7:
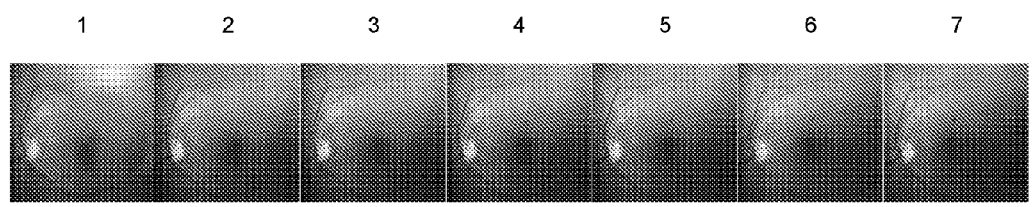
FIG. 7 illustrates a sequence of retinal images recorded by an embodiment of the invention following photo-bleaching.

FIG. 6 shows a short sequence of images taken in step 420 using 590 nm illumination after 20 minutes of dark adaptation in step 410. FIG. 7 shows sequence of images obtained approximately 20 seconds after a 60 second period of bleaching in step 430 that bleached approximately 92% cone and 84% rod photo-pigment bleach. A mean grey scale value for the sequences changes from 84.41 for the dark adapted images to 86.16 for the light adapted images i.e. ~2% lighter than the dark adapted images. This suggests the mean optical density of the photo-pigments at this wavelength across the retina is 0.0089.

Figure 8:
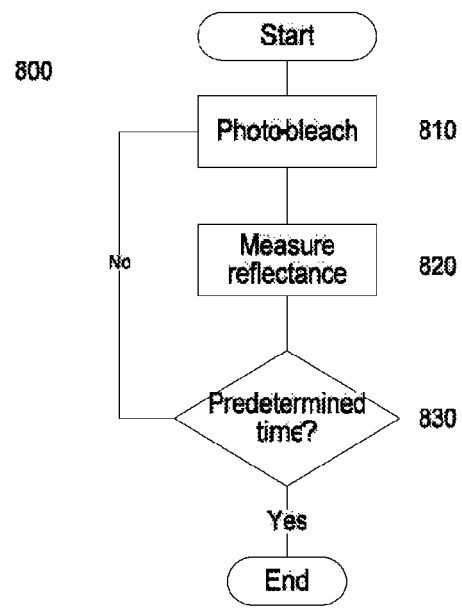
FIG. 8 illustrates a method according to a second embodiment of the invention.
Figure 9:
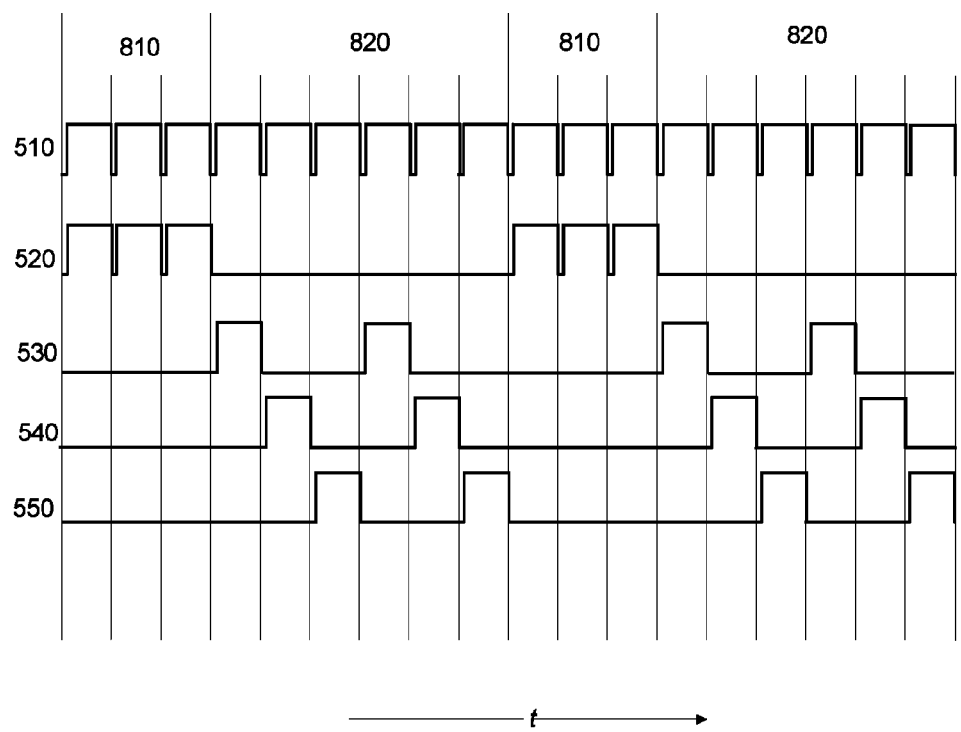
FIG. 9 illustrates a timing diagram according to an embodiment of the invention.

FIGS. 8 and 9 illustrate a method 800 according to the second embodiment of the invention.

In the method according to the second embodiment the light sources operate in a rapid "flicker" mode. In particular, the bleaching module 130 is arranged to output bleaching illumination in short pulses. In some embodiments the pulses of bleaching illumination are 50 ms in duration. However the pulses may be up to 100 ms, up to 500 ms, or up to 15 seconds in duration. In some embodiments, the pulses of bleaching illumination are output at a frequency of 1 Hz, although it will be realised that other frequencies may be envisaged. This mode of operation contrasts from that described with reference to FIGS. 4 and 5 wherein the bleaching illumination was output in a substantially continuous manner for a period of time e.g. 30 seconds during step 430. In the present mode, bleaching illumination is output in relatively short pulses, such that the bleaching illumination has a duty cycle of less than 20%, less than 10% or around 5%. The method according to the present invention is intended to evaluate short term changes in eye reflectance brought about in response to flickering bleaching stimuli. Following one or more pulses of bleaching illumination, images recording reflectance of the eye at one or more wavelengths of reflectance illumination are recorded.

Referring to FIG. 8, in step 810 a pulse of light for partially photo-bleaching the eye is delivered to the eye. As previously explained the pulse of light is generated by the bleaching unit 130 and communicated to the head unit 102 before being directed to the eye. The pulse may be a 50 ms pulse of bleaching illumination. FIG. 9 illustrates control signals in the apparatus as explained previously with reference to FIG. 5 and signals having like reference numerals have the same purpose. It will be noted that FIG. 9 is not drawn to scale. The bleaching illumination is controlled according to the bleaching signal 520. Following the bleaching illumination, the image transfer signal 510 is operable (low) during which stored charge corresponding to an image is transferred to the storage portion. It will be noted that this image corresponds to reflected bleaching illumination and may be omitted in some embodiments.

In step 820 each of the reflectance light sources controlled by the reflectance signals 530-560 is operably controlled to be active for a predetermined period whilst a corresponding image is recorded. The predetermined period may be the same as the duration of the bleaching pulse in step 810, although in other embodiments the pulses of reflectance illumination may be of other duration sufficient to determine the reflectance of the eye at that wavelength. Thus in step 820 reflectance of the eye is determined at one or more wavelengths.

In step 830 it is determined whether the method has been performed for a predetermined measurement time. The measurement time may be set by the operator using the graphical user interface as described above. If the measurement method has not been performed for the predetermined time then the method returns to step 810, whereas if the measurement time has been reached the method ends.

During optional step 810, particularly following step 830, there may be a period during which the eye is not subjected to illumination from the apparatus. For example, if the bleaching and reflectance measurement process of steps 810 and 820 takes 250 ms and step 810 is to be performed at a frequency of 1 Hz then there may be a period of 750 ms during which no illumination is generated. During this period images of the eye may still optionally be recorded in some embodiments.

The predetermined time for which step 810-820 are performed may be 1 minute, two minutes or another selected duration. However it will be appreciated that the method illustrated in FIGS. 8 and 9 may be substantially quicker than that illustrated in FIGS. 4 and 5.

In some embodiments of the invention, the analysis unit 103 arranged to determine an average reflectance value across a plurality of images. The average reflectance value may be determined for one or more wavelengths of reflectance illumination. For example, the analysis unit may be arranged to determine an average reflectance value across 10, 20, 50, 100 or 200 images at one or more wavelengths. The average reflectance value may be determined for each pixel in the images i.e. so that an average reflectance value for that pixel is determined from a plurality of images. It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A retinal densitometer, comprising:
   an illumination unit configured to output bleaching illumination for photo-bleaching an eye and reflectance illumination at a plurality of wavelengths for determining reflectance of the eye at each of the plurality of wavelengths;
   an imaging device configured to output image data corresponding to an image of the eye at each of the plurality of wavelengths of reflectance illumination; and
   a control unit configured to control the illumination unit and the imaging device to output the bleaching illumination, the reflectance illumination at the plurality of wavelengths, and the image data according to a predetermined sequence;
   wherein the control unit is configured to control the illumination unit to output the bleaching illumination during a photo-bleaching period preceding a dark recovery period;
   wherein the control unit is configured to control the illumination unit to output the reflectance illumination during the dark recovery period and to control the imaging device to periodically output image data corresponding to the reflectance illumination reflected from the eye, wherein during the dark recovery period the illumination unit is controlled by the control unit to sequentially output the reflectance illumination at each of the plurality of wavelengths according to the predetermined sequence; and
   wherein the control unit is configured to control the illumination unit to repeatedly output the predetermined sequence of reflectance illumination and to control the imaging device to output image data corresponding to the reflectance illumination at each wavelength.

2. The densitometer of claim 1, wherein the control unit is configured to control the illumination unit and the imaging device according to the predetermined sequence to output image data indicative of the reflectance of the eye at each of the plurality of wavelengths.

3. The densitometer of claim 1, wherein the image data is indicative of the reflectance of the eye at each of the plurality of wavelengths at each of a plurality of times throughout the dark recovery period.

4. The densitometer of claim 3, wherein the image data is indicative of the reflectance of at least a region of the eye at each of the plurality of times.

5. The densitometer of claim 1, wherein the image data comprises reflectance values at each of a plurality of locations distributed over the eye.

6. The densitometer of claim 1, wherein the image data is indicative of changes in reflectance of the eye during the dark recovery period.

7. The densitometer of claim 1, comprising an analysis unit configured to determine a reflectance value for each of the plurality of wavelengths based on image data representing a plurality of images of the eye over the dark recovery period.

8. The densitometer of claim 7, wherein the reflectance value is an average reflectance value.

9. The densitometer of claim 1, wherein the control unit is configured to cause the illumination unit and the imaging device to repeatedly output image data corresponding to the reflected illumination at each of the plurality of wavelengths at predetermined intervals.

10. The densitometer of claim 1, wherein the photo-bleaching period is sufficient to cause substantial photo-bleaching of the eye.

11. The densitometer of claim 1, wherein the photo-bleaching period has a duration of 2 minutes or greater.

12. The densitometer of claim 1, wherein the control unit is configured to cause the illumination unit to output the bleaching illumination in a flicker mode.

13. The densitometer of claim 12, wherein in said flicker mode the illumination unit outputs the bleaching illumination in pulses having a duration of up to 15 seconds.

14. The densitometer of claim 13, wherein the pulses have a duration of up to 1 second.

15. The densitometer of claim 13, wherein the pulses have a duration of up to 0.5 or 0.2 seconds.

16. The densitometer of claim 12, wherein in the flicker mode the illumination unit is controlled to output the bleaching illumination in pulses and the control unit is configured to cause the imaging device to output image data corresponding to reflected illumination at one or more wavelengths during a reflectance measurement period between at least some of the pulses of bleaching illumination.

17. The densitometer of claim 16, wherein the control unit is configured to cause the illumination unit to output reflectance illumination during the reflectance measurement period according to the predetermined sequence.

18. The densitometer of claim 16, wherein the illumination unit is controlled to output the reflectance illumination at a plurality of wavelengths during the reflectance measurement period.

19. The densitometer of claim 16, wherein the illumination unit is controlled to sequentially output the reflectance illumination at each of a plurality of wavelengths during the reflectance measurement period.

20. The densitometer of claim 16, wherein the control unit is configured to cause the imaging device to output image data corresponding to reflected illumination at the plurality of wavelengths.

21. The densitometer of claim 12, wherein in the flicker mode the control unit is configured to control the illumination unit and the imaging device to repeatedly perform the reflectance measurement period between at least some pulses of bleaching illumination.

22. The densitometer of claim 12, wherein an average reflectance is determined based upon a plurality of images at each of one or more wavelengths of reflectance illumination.

23. The densitometer of claim 1, comprising a head unit having optics for directing the bleaching and reflectance illumination to the eye, and for receiving reflected illumination from the eye.

24. The densitometer of claim 23, wherein the optics are configured to direct the bleaching and reflectance illumination and to receive reflected illumination from separate regions of a pupil.

25. The densitometer of claim 1, wherein the image data corresponds to an image of light reflected from a predetermined region of the retina.

26. The densitometer of claim 1, wherein the predetermined region is substantially stationary with respect to the eye.

27. A densitometery method, comprising:
   outputting photo-bleaching illumination for photo-bleaching an eye during a photo-bleaching period preceding a dark recovery period;
   outputting reflectance illumination for determining reflectance of an eye at each of a plurality of wavelengths according to a predetermined sequence during the dark recovery period, wherein during the dark recovery period the reflectance illumination is repeatedly output at each of the plurality of wavelengths according to the predetermined sequence; and
   storing image data corresponding to an image of the eye at each of the plurality of wavelengths during the dark recovery period.

28. The method of claim 27, comprising storing image data at predetermined intervals during the dark recovery period.

29. The method of claim 28, wherein the image data stored at the predetermined intervals is indicative of the reflectance of the eye at the predetermined intervals during the dark recovery period.

30. The method of claim 27, wherein the photo-bleaching illumination is output in pulses of a predetermined duration.

31. The method of claim 30, wherein the reflectance illumination is output and the images are stored between at least some of the pulses of photo-bleaching illumination.

32. The method of claim 31, comprising determining an average reflectance value based on a plurality of images at each of one or more wavelengths of reflectance illumination.

33. The method of claim 30, wherein the pulses have a duration of less than 5 seconds.

* * * * *